United States Patent [19]

Burnett

[11] 4,122,836
[45] Oct. 31, 1978

[54] SHIELDING HOLDER FOR RADIONUCLID SYRINGES

[75] Inventor: Thomas W. Burnett, Bellevue, Wash.

[73] Assignee: Nuclear Pacific, Inc., Seattle, Wash.

[21] Appl. No.: 722,538

[22] Filed: Sep. 13, 1976

[51] Int. Cl.² .............................................. A61N 5/12
[52] U.S. Cl. ...................................... 128/1.1; 128/215
[58] Field of Search ............ 128/1.1, 2 A, 215, 218 R, 128/218 A, 218 C, 218 D; 250/506, 512, 513, 515

[56] References Cited

U.S. PATENT DOCUMENTS

| | | | |
|---|---|---|---|
| 3,596,659 | 8/1971 | Glasser | 128/215 |
| 3,623,474 | 11/1971 | Heilman et al. | 128/2 A |
| 3,769,490 | 10/1973 | Czaplinski | 250/506 X |
| 3,820,541 | 6/1974 | Langan | 128/1.1 X |

*Primary Examiner*—John D. Yasko
*Attorney, Agent, or Firm*—Christensen, O'Connor, Johnson & Kindness

[57] ABSTRACT

A full viewing shielding holder for radionuclid disposable plastic syringes is disclosed. Maximum light gathering for illumination of the syringe scale and clear visibility of that scale in any relatively rotated position of the holder and of the syringe therein are afforded by the improved holder comprising a tubular body of radiation shielding glass translucent and optically polished substantially throughout its circumference and length and having a quickly engageable and disengageable syringe gripping means fitted on one end thereof. In one disclosed embodiment the releasable gripping means comprises a rubber "O"-ring compressible against the syringe body by a clamping means to hold the syringe in place by friction. In a second embodiment the releasable gripping means comprises an internally threaded fitting cooperating with an element on the syringe. When the syringe is inserted into the holder, a slightly tapered annular flange on the end of the syringe enters the fitting snugly, whereupon turning of the syringe with insertion pressure continued causes self-threading of the fitting in the soft flange material to hold the syringe releasably.

5 Claims, 4 Drawing Figures

SHIELDING HOLDER FOR RADIONUCLID SYRINGES

BACKGROUND OF THE INVENTION

This invention relates to an improved shielding holder for radionuclid injection syringes such as the disposable polyethylene syringes currently being used for injecting radioactive substances into a patient's bloodstream for diagnostic or therapeutic purposes. The primary object of the invention is to minimize the radiation exposure to which the technician is subjected in utilizing such a radionuclid syringe while providing for the convenient installation, reliably safe use and easy removability of a syringe from the holder for disposal after use. The invention is herein illustratively described by reference to the presently preferred embodiments thereof; however it will be recognized that certain modifications and changes therein may be made with respect to details without departing from the essential features involved.

The need for more convenient and more safely reliable shielding holders for disposable radionuclid syringes has increased with the expansion of nuclear medicine and the increased emphasis on minimizing radiation exposure of the doctor or technician. With such disposable syringes, typically made of synthetic plastics materials such as polyethylene, radiation shielding by the wall of the syringe body itself is insignificant. Consequently reliance for shielding is placed primarily upon the syringe holder.

It is thus of fundamental importance to design the holder so as to minimize the total dosage of radiation to which the technician is subjected during an injection procedure. Dosage in turn is a function of unabsorbed radiation intensity and exposure time. Exposure time in this case starts with drawing into the syringe a measured amount of radionuclid liquid from a supply container, continues through the process of injecting a measured amount of the radionuclid into the patient's bloodstream and terminates with the steps of releasing of the syringe from the holder, disposal of the used syringe and placement of the holder in a suitable repository for subsequent cleansing. The companion factor determining technician exposure, namely intensity of unabsorbed radiation reaching the technician, is governed by specific absorption of the shielding material and the thickness of that material. Given the type of holder material to be used, however, there are practical limitations on holder wall thickness because of the weight factor and also because of the interference that an unduly thick holder presents in attempting to position the syringe at the necessary shallow angle of incidence to the patient's skin in order to penetrate the vein properly.

In achieving its objectives this invention, while providing a shielding holder of acceptable weight and thickness for suitable handling characteristics, hence one having limited shielding effect, compensates for that limitation by the reduction of technician exposure time it makes possible. As a major contribution in that regard, the improved holder enhances the illumination and visibility of syringe contents and related scale markings so as to facilitate its convenient use with safely reliable accuracy under all working light conditions and without necessity of critical positioning of the holder or of the syringe in the holder for viewing by the technician. In this way the improved holder greatly reduces the chance of quantitative error in the use of the syringe attributable to poor visibility of the radionuclid syringe contents and graduation marks as compared with prior types of holders, especially when used under restricted ambient light conditions or when the user is tired or otherwise not at peak performance.

Prior attempts to provide shielding holders for radionuclid syringes have stressed principally the shielding factor through use of heavy metal holder bodies provided with narrow viewing windows or glass filled slits for observation of the syringe contents and its scale graduation marks. An example is to be found in the disclosure of U.S. Pat. No. 3,596,659. However, such holders, although heavy and cumbersome, are still lacking in shielding capability, and are not easy to use conveniently and with quick efficiency because of viewing difficulties. The steel or lead body of the holder excluding all ambient light except that which can enter through the glass window or slit, makes it often necessary to position the holder with the slit facing as nearly as possible toward the main source of light, and even then the interior of the holder is quite dark and partly masked by reflected light. Moreover if the scale of graduations on the syringe are to be seen clearly through the slit window it is often necessary to rotate the syringe until such graduations make their clearest appearance. These steps and precautions take time and thereby impede the operation, and unless care is taken in this way to secure the clearest attainable view, a mistake can be made either during loading of the syringe or during the injection that follows. Furthermore it is difficult in such cases to mount and seal the glass to the slitted steel or lead sleeve in a manner preventing radiation leakage at the interface. It will be appreciated therefore that the advantage of a dense metal shield in such prior holders can be more than offset by other factors and in the end leave the technician subjected to excessive dosage of radiation and the patient to the possibility of errors due to limited visibility of syringe contents and graduation marks.

BRIEF DESCRIPTION OF INVENTION

In accordance with this invention as herein disclosed the syringe is removably gripped in a full viewing shielding holder comprising a lead glass tubular body that is both translucent and optically polished substantially throughout its circumference and length and that is provided with a readily releasable gripping means fitted on one end and quickly operable so as to grip and hold the syringe securely against shifting in the holder when the syringe is being operated by the technician either to withdraw radionuclid from a source vial or to inject the radionuclid into the patient's bloodstream.

With such a holder it becomes practicable to achieve a radiation attenuation factor of 75, compared with 40 to 50 for most competitive holders available commercially, and in addition to greatly reduce the technician's radiation exposure time while enhancing the safely reliable accuracy of the technician using the held syringe. The lead glass wall being translucent throughout admits light omnidirectionally in such manner as to fully illuminate the syringe, including its contents and its graduation marks within the holder. Moreover, rotative orientation of the holder in relation to the primary light source or in relation to the viewer's eye becomes noncritical as does the relative rotative orientation of the syringe within the holder. Hence, at a glance the technician drawing radionuclid from a septum-sealed vial can gauge the amount withdrawn and as quickly and conveniently can reliably gauge the amount injected into the patient with minimal chance of error under any working light conditions. Furthermore it is found that a lead glass holder wall thickness of very slightly in excess of ¼ inch using lead glass of a specific density in the range of 4.2 to 7.0 is adequate (providing a radiation attenuation factor of up to approximately 75) without creating a holder of undue weight nor one of such large diameter as to interfere with proper aspect orientation of the syringe needle to the patient's skin during venipuncture.

These and other features, objects and advantages of the invention will become more fully evident from the following description thereof by reference to the preferred embodiments shown in the accompanying drawings and hereinafter described.

DETAILED DESCRIPTION

Figure 1:
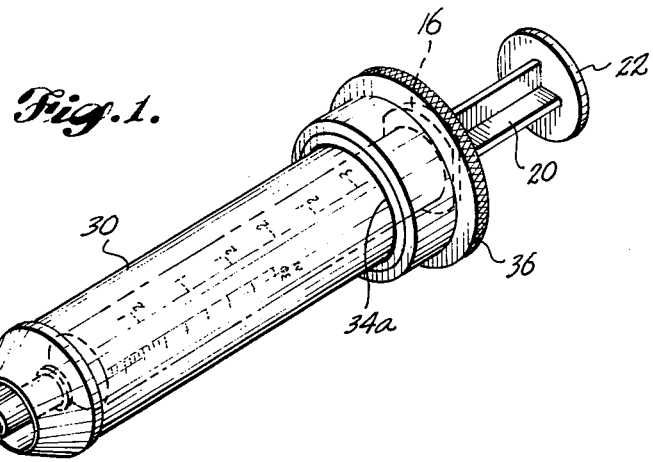
FIG. 1 is a prospective view of the improved syringe holder in one form.
Figure 2:
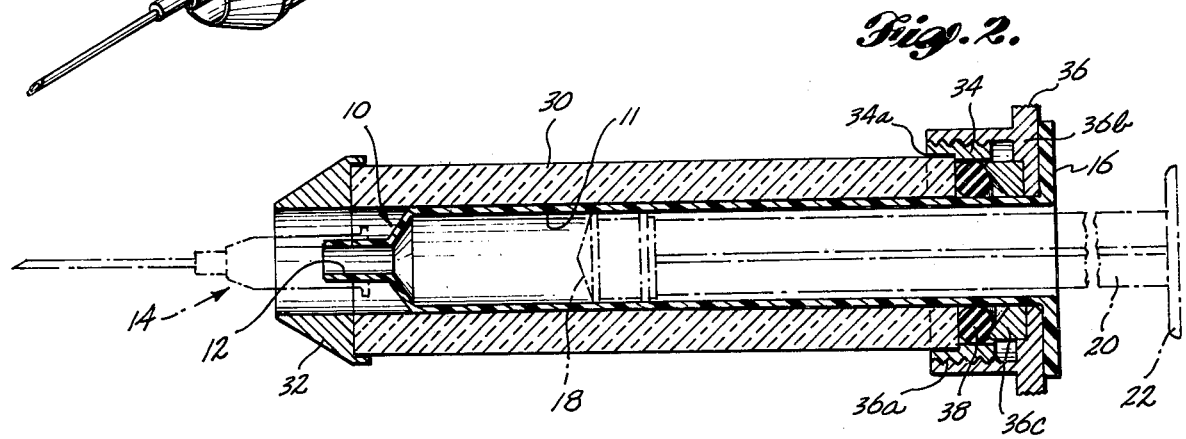
FIG. 2 is a longitudinal sectional view of the holder shown in FIG. 1 at slightly enlarged scale, in each instance a syringe being illustrated installed in the holder.

In FIGS. 1 and 2 syringe 10 is of typical make-up and form, including an elongated tubular body 11 that, after a steeply tapered step reduction in diameter, terminates in a discharge nozzle 12. Nozzle 12 is adapted to receive and hold the base of an injection needle assembly 14. The syringe body has a radial flange or stop 16 at its opposite end and a plunger piston 18 backed by a plunger rod 20 that terminates in an actuator cap 22. Graduation marks (not shown) are provided in a scale along the syringe body that itself is transparent to a degree permitting viewing of the contents of the syringe and detecting the presence of air bubbles if they occur.

The illustrated syringe 10 or one similar to its may be quickly installed in the holder of FIGS. 1 and 2 by simply inserting the syringe lengthwise therein, nozzle end foremost, until the stop 16 comes into abutment with the end fitting of the holder. The illustrated holder comprises a lead glass tubular body 30 that is both transparent and optically polished throughout its circumference and length. Preferably the tubular body 30 is formed of lead glass of a specific density in the range of 4.2 to 7.0 and of a wall thickness adequate for mechanical strength and radiation absorptivity. As a typical example, with a specific density of 7.0 and a wall thickness of ¼ inch, as presently preferred, the holder provides an attenuation factor of 75.

The length of lead glass body 30 is sufficient not only to house the syringe but to reveal substantially the full length of the syringe cylinder therewithin. The syringe body fits slideably within the interior of the holder body 30 and is preferably terminated at its discharge end by a heavy metal fitting 32, such as one of copper or brass, bevel-tapered to its extremity and epoxy resin bonded to the end face and adjacent peripheral extremity of the glass body 30.

At its opposite end the shielding holder body 30 of FIGS. 1 and 2 carries a quickly disengageable and engageable syringe gripping means fitted thereto. Such gripping means includes an exteriorly threaded ring 34 having a shallow locating notch 34a therein and epoxy resin bonded to the surfaces of the glass contacted by the notch walls. It further includes a knurled rotative collar 36 having a sleeve portion 36a internally threaded to engage the threads of the fixed ring 34. Opposite the sleeve portion 36a, the collar 36 also carries an inwardly directed end flange 36b that mounts a wedging ring 36c with a longitudinally facing wedging surface that diverges inwardly of the assembly, i.e., toward the discharge end of the syringe holder. A rubber-like "O"-ring 38 is interposed between the wedging ring and the opposing end wall of the syringe holder body 30. Rotation of threaded collar 36 to advance the wedging ring 36c so as to clamp and compress the rubber tubular "O"-ring 38 against the end wall of the tubular holder body 30 forces the "O"-ring to bulge radially inwardly so as to exert increasing constriction pressure around and against the wall of the syringe. In this manner the syringe can be firmly gripped and held by friction as tightly as desired. Releasing the syringe for removal from the holder is carried out as quickly and easily by reversely turning the collar 36. If desired, abrasive grit may be embodied in the rubber or rubber-like material comprising the "O"-ring 38 in order to improve the grip when the "O"-ring is under clamping pressure.

In operation, once the syringe is firmly locked in the holder as shown in FIGS. 1 and 2, the syringe plunger 18 is advanced in the usual manner to the discharge end of the syringe, the syringe needle is inserted through a suitable septum in a vial containing radionuclid liquid and thereupon the syringe knob is drawn back until the correct amount of radionuclid is sucked into the syringe as revealed by graduation marks on the syringe body. These are well illuminated under any working light conditions and viewed readily through the transparent full viewing holder tube 30, and from any direction regardless of rotative orientation of the holder or of the syringe in the holder.

The technician thereupon may place the syringe holder and syringe assembly close along side the patient's body to advance the needle into the vein at the desired shallow angle of incidence. Chamfering or taper of the end of holder fitting 32 facilitates close positioning of the adjacent end of the holder to the patient's body. Upon injecting the required amount of radionuclid into the patient's vein, as readily determined by observing the clearly visible syringe graduation marks through the holder wall, the clamping collar can be quickly released to permit removing the syringe for disposal.

Figure 3:
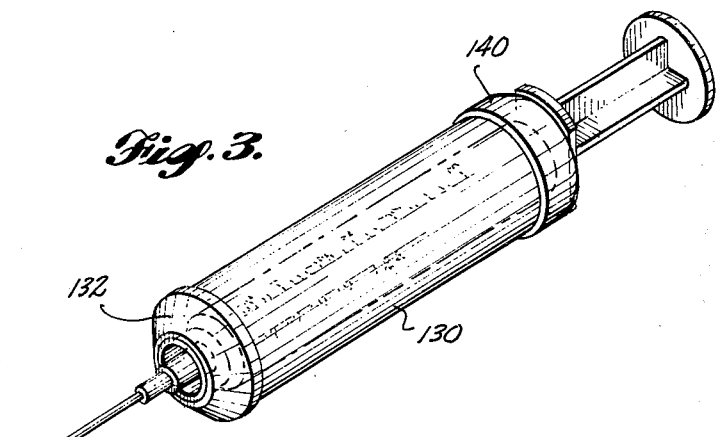
FIG. 3 is a view similar to FIG. 1 of a modified holder.
Figure 4:
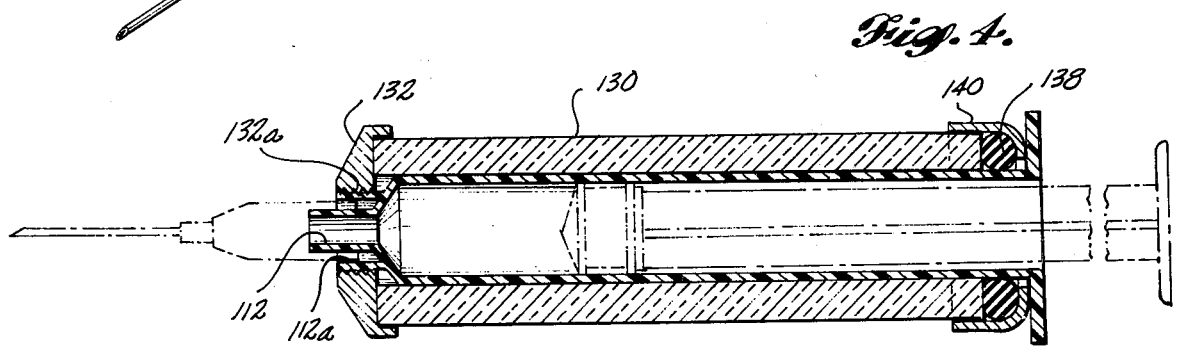
FIG. 4 is a sectional view similar to FIG. 2 showing the modified holder.

In the embodiment shown in FIGS. 3 and 4 retention of the syringe in the holder is accomplished in a somewhat different manner, made possible by the somewhat modified form of the syringe itself. In this case the discharge end of the syringe has a slightly tapered end sleeve 112a surrounding its nozzle 112. Sleeve 112a is slightly smaller in diameter than that of the syringe body and somewhat larger in diameter than that of the syringe nozzle 112. The adjacent end of the holder in this case comprises a fitting 132 that is epoxy bonded to the end of the tubular body 130 and that has an interior tubular wall with a sharp spiral thread 132a. The thread tip diameter is slightly smaller than the outer diameter of sleeve 112a at its leading end to be inserted into fitting 132. However, by rotating the syringe in the proper direction as it is being pressed into the holder, the thread 132a bites into the sleeve 112a in a "self-threading" action so as to form a grip or lock on the syringe. Release of the syringe for removal from the holder is then easily accomplished simply by pulling and reversely turning the syringe in relation to the holder 130. Pitch of the thread 132a may be relatively steep so as to minimize the total turning of the syringe to bring it to a full seat in the fitting 132.

The opposite end of the holder in this second embodiment has a rubber "O"-ring 138 held in place by a retention cap 140 that is epoxy bonded to the end of the holder tube 130. This "O"-ring 138 has an inside diameter not materially larger nor smaller than the exterior diameter of the syringe wall that can thereby serve as an entrance guide and centering stabilizer; if desired, as a low-resistance frictional restraint for the syringe being moved into and out of the holder. However, it is not necessary to rely upon the rubber "O"-ring 138 in order to hold the syringe firmly in place.

What is claimed is:

1. A full-viewing shielding holder for radionuclid injection syringes comprising a tubular body of radiation shielding glass transparent and optically polished substantially throughout its circumference and length adapted to gather light omnidirectionally and to reveal syringe contents and syringe graduation marks with the syringe extending longitudinally through said tubular body independently of its relative rotated position in said tubular body and of the tubular body's rotated position relative to the viewer, manually releasable gripping means fitted on one end of said tubular body manually operable to grip and hold the syringe against shifting therein when the syringe is being operated in the holder, said gripping means comprising an elastic ring positioned to closely encircle the syringe adjacent one end of the tubular body, and retainer means including annular clamping means manually operable to compress the elastic ring and constrict the same under pressure against the syringe and to release the syringe thereafter from such pressure.

2. The holder defined in claim 1, wherein the clamping means comprises threaded elements, one fixed to the tubular body, interengageable, to effect relative longitudinal approach and separation between such elements by relative rotation therebetween, and a wedging ring interposed within one such element having a tapered annular surface engaging said elastic ring and sloped to effect longitudinally and radially inward compression of such ring by relative approach between such elements.

3. A full-viewing shielding holder for radionuclid injection syringes comprising a tubular body of radiation shielding glass transparent and optically polished substantially throughout its circumference and length adapted to gather light omnidirectionally and to reveal syringe contents and syringe graduation marks with the syringe extending longitudinally through said tubular body independently of its relative rotated position in said tubular body and of the tubular body's rotated position relative to the viewer, and manually releasable gripping means fitted on one end of said tubular body manually operable to grip and hold the syringe against shifting therein when the syringe is being operated in the holder, said holder being engageable with a syringe of a type having a cylindrical surface tapering slightly toward one end, said gripping means comprising an annular fitting having a thread element inside the same with an edge sharpened to indent said syringe cylindrical surface when pressed against the same so as to grip and hold the same upon combined forcibly advancing and turning of the syringe relative to the tubular body.

4. The holder defined in claim 1 whereby the elastic ring is impregnated with an abrasive grit.

5. The holder defined in claim 3 and means on the opposite end of the tubular body including a rubber-like "O"-ring and retainer means therefor, said "O"-ring slideably engageable with the tubular body.

* * * * *